United States Patent [19]
Rutz

[11] 4,167,253
[45] Sep. 11, 1979

[54] DISPENSER

[76] Inventor: Almer J. Rutz, Box 816, Riverdale, N. Dak. 58565

[21] Appl. No.: 847,758

[22] Filed: Nov. 2, 1977

[51] Int. Cl.² .............................................. B65H 19/00
[52] U.S. Cl. ..................................... 242/55.53; 242/60
[58] Field of Search ............... 242/55.53, 60, 71, 71.1, 242/71.7, 134–138; 312/39; 225/46, 47, 57–67; 206/824, 389, 397, 409; 221/312 C, 197

[56] References Cited
U.S. PATENT DOCUMENTS

| | | | |
|---|---|---|---|
| 3,405,983 | 10/1968 | Rutz | 312/39 |
| 3,945,584 | 3/1976 | Mangan | 242/71.1 |
| 4,034,926 | 7/1977 | Wegner | 242/55.53 |

*Primary Examiner*—Leonard D. Christian
*Attorney, Agent, or Firm*—Robert E. Kleve

[57] ABSTRACT

A bandage roll dispenser comprising a front and rear housing adapted to be slidably fitted together. The front half has a horizontal channel and a front half of a spool housing. The front half of the spool housing has slots therein. A rod of bandage has a center roll therein. The center rod is adapted to be mounted in the slots of the front half of the spool housing with the roll of bandage mounted therein. The horizontal channel is adapted to receive the outer end of the roll of bandage. The rear half of the spool has a plate adapted to be slid over the end of the gauze and over the horizontal channel. The rear half of the spool housing also has a rear half a spool housing adapted to abutt the front half of spool housing.

2 Claims, 8 Drawing Figures

U.S. Patent  Sep. 11, 1979  4,167,253
FIG. 1.
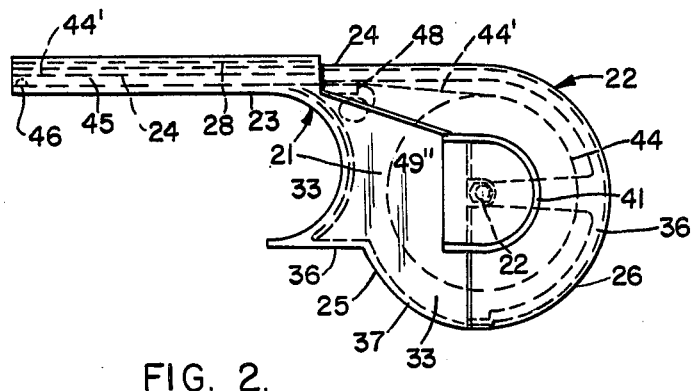
FIG. 2.
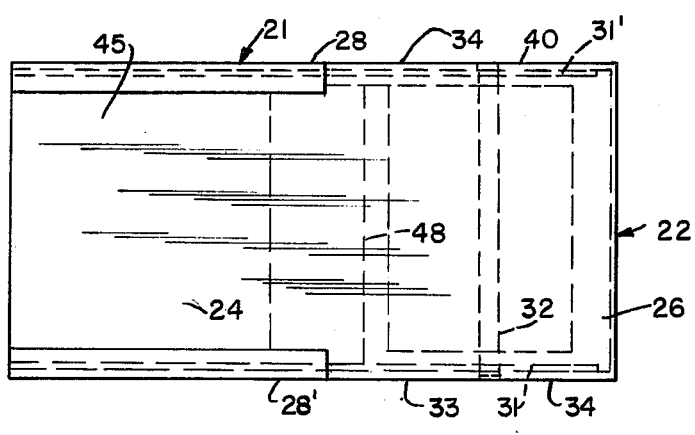
FIG. 7.
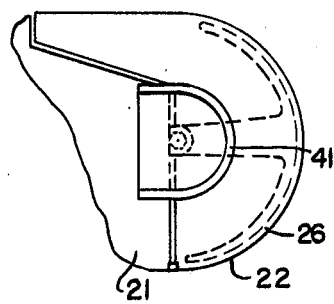
FIG. 8.
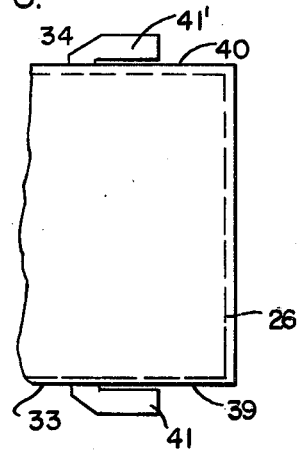
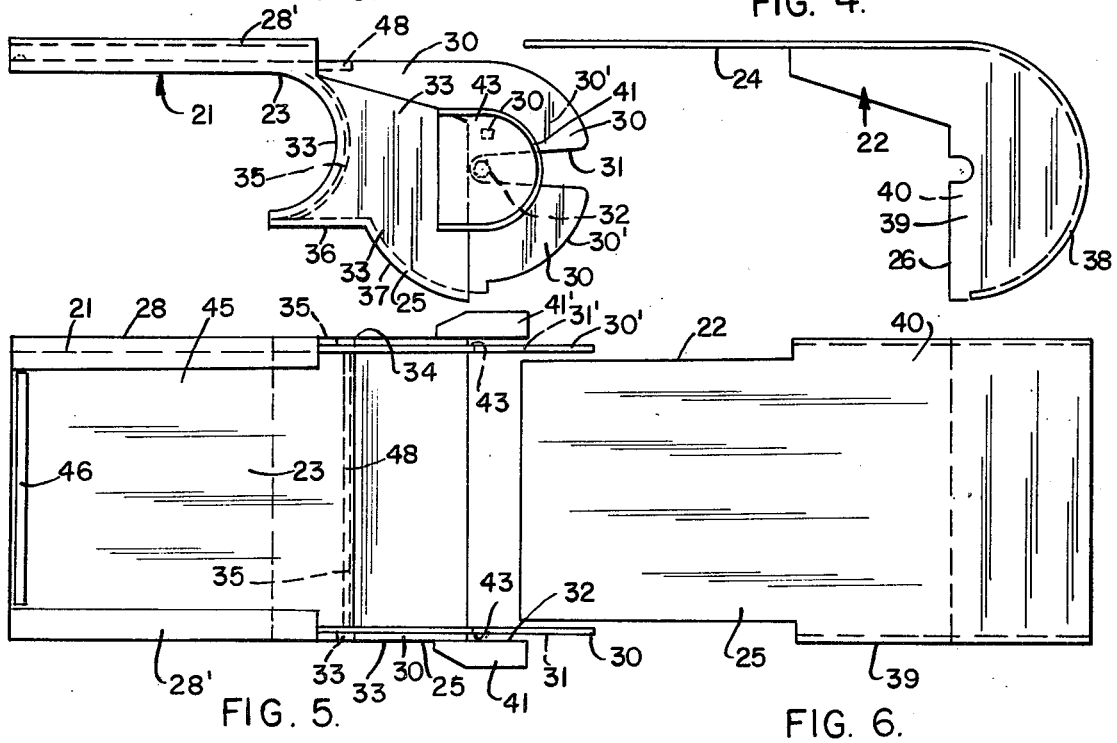
FIG. 3.  FIG. 4.
FIG. 5.  FIG. 6.

DISPENSER

This invention relates to bandage dispensers.

It is an object of the invention to provide a novel bandage dispenser for dispensing a roll of bandage that can be easily separated and reassembled to replace the roll of bandage.

It is another object of the invention to provide a novel roll of bandage or roll of gauze dispenser which can be easily operated to unroll the bandage and wind or wrap it in a selected manner.

Further objects and advantages of the invention will become apparent as the description proceeds and when taken in conjunction with the accompanying drawing wherein:

FIG. 1 a side elevational view of the roll of gauze or bandage dispenser with the dispenser assembled and a roll of bandage therein.

FIG. 2 is a top plan view of the roll of gauze or bandage dispenser with the dispenser assembled and a roll of bandage therein.

FIG. 3 is a side elevational view of the roll of the forward half of the gauze or bandage dispenser with the dispenser disassembled.

FIG. 4 is a side elevational view of the roll of the rearward half of the gauze or bandage dispenser with the dispenser disassembled.

FIG. 5 is a top plan view of the forward half of the gauze or bandage dispenser.

FIG. 6 is a top plan view of the rearward half of the gauze or bandage dispenser.

FIG. 7 is a fragmentary side view of the dispenser illustrating one of the finger grips.

FIG. 8 is a fragmentary top plan view of the dispenser with the finger grips attached and the dispenser assembled.

Briefly stated the invention comprises a roll of gauze or bandage dispenser comprising a front and rear housing adapted to be fitted together with a roll of bandage therein. The front housing has a front half of a spool housing to receive the front half of the roll of bandage and a horizontal plate to receive the outer end of the roll of bandage. The rear housing has a horizontal plate to overlie the outer end of the roll of bandage and the horizontal plate. The rear housing also has a rear half of a spool housing to receive the rear half of the roll of bandage. The housings also have flange means to interlock the housings together.

Referring more particularly to the drawing in FIG. 1, the invention 20 is illustrated as having a two part housing construction of a forward channel and front half of the spool housing 21 and a forward extending plate and rear half of the spool housing 22. The forward channel 23 of the housing 21 is adapted to receive the plate 24 of the housing 22 and the forward half 25 of the spool portion of the housing 21 is adapted to receive the rearward half 26 of the spool housing 22.

The forward housing 21 has inturned flanges 27 and 28 to overlap the plate 24 when the plate 24 is slidably received in the channel. The forward half 25 of the spool portion of housing 21 has set in flanges 30 and 30' along the rear edge which extend rearward and act to form a second rear spool housing and are formed integrally to the housing 21. The set in flanges 30 and 30' are adapted to be slidably received into the rearward half 26 of the spool portion of the housing 22. The set in flanges 30 and 30' and a portion of the forward half 25 of the spool housing have a pair of elongated notches 31 and 31' to receive a rod 32 to support the rod in the spool housing 25 when the two parts of the housing are assembled, as shown in FIGS. 1 and 2, with a roll of bandage 44 mounted on the rod 32 and enclosed in the two parts of the housing, as illustrated in FIGS. 1 and 2.

The flange 30 is set in from the main side flange portion 33 of housing 21. The flange 30' is set in from the main side flange portion 34 of housing 21. The forward housing has a curved half cylindrical front portion 35 fixed between the main flange portions 33 and 34 and recessed rearwardly slightly from the curved forward edge 33' and 34' of main flange portions 33 and 34. The forward housing has a flat bottom wall portion 36 and a cylindrical bottom wall 37 fixed between flanges 33 and 34 to close the bottom of the forward half of the housing. The rear housing 22 has a curved cylindrical back wall 38 and side flanges 39 and 40. The side flanges 39 and 40 are fixed between edges of the plate 24 and back wall 38.

The device 20 has a pair of finger grips 41 and 41' fixed to the main side flanges 33 and 34 to the front half 25 of the spool housing. Each finger grip has a base portion 41' and an annular channel wall 41" fixed about the base portion 41'. The side flanges 39 and 40 of the rear half 26 of the spool housing slide over the flat set in flanges 30 and 30' between the finger grips 41 and 41' in the space 32 therebetween to attach housing 22 and 21. A raised cam surface 43 on set in flanges 30 and 30' serves as a cam to lock the side flanges 39 and 40 to flanges 30 and 30' in their attached position of housing 21 and 22, shown in FIG. 1. The base 45 of the channel 23 has a raised ridge 46. The base 45 also has a projecting rearward plate 48.

The device will receive a roll 44 of hospital bandage material or gauze having a center rod 32 into the housing by the rod 32 being inserted into the slots 31 and 31' of flanges 30 and 30' from left to right when viewed from FIG. 3, to position the roll and rod in the position shown in FIGS. 1 and 3. The outer end 44' of the roll of gauze 44 will extend up and into the base 45 of the channel 23 between the base 45 and overlapping plate 24. The gauze will be fed outward from between the front channel 23 and the overlapping plate 24.

The device is employed normally to wrap bandage material about the arms and legs and other portions of the body by placing the end 44' of the roll of bandage 44 on the member of the body to be wrapped and holding it there with one hand, and then with the other hand, while holding the device in the finger grips by two fingers, or while holding the device with one finger of the other hand in the channel member 35, and then rotating the device about the arm, for example, while holding the outer end of the roll of bandage or gauze to the arm. This causes the gauze or bandage to feed out of the device by its unrolling from the roll therein, to wind or wrap the gauze onto the arm.

The two part construction of the device makes it easier to replace the roll of bandage or gauze simply by separating the two parts 21 and 22 and inserting a rod 32 into the center of the new roll of bandage and then the new roll of gauze is placed into the forward half of the spool housing by inserting the rod 32 into the notches or slots 31 and 31' to their position shown in FIGS. 1 and 2 and placing the end 44' of the roll of gauze in base 45 the front channel 23, and then inserting the rear half 22 of the housing into the front half 21, and by inserting the plate 24 into the channel 23 on top of the end 44' of the gauze and inserting the rear half 26 of the spool over the set in flanges 30 and 30' at the front half of the spool to place the two parts of the housing together, as illustrated in FIGS. 1 and 2.

The plates 39 and 40 of the housing 22 have identical notches 39' and 40' to enable the plates 39 and 40 to extend about rod 32 when housing 22 is attached to housing 21.

As the gauze is dispensed out the front of the device, the raised ridge 46 acts to frictionally engage the gauze against the underside of plate 24 to provide a drag on the gauze so that the gauze will not run freely out of the dispenser, but requires a small amount of force on the gauze relative to the dispenser. The raised rib 46 acts frictionally to engage the gauze against the underside of plate 24. The ridge 46 on the base 45 provides enough drag on the gauze so that the dispenser and gauze may be suspended in air by merely holding it in air by the outer end 51 of the gauze. The gauze will not run out of the dispenser thus suspending the dispenser in air.

A roll of gauze may be used in the dispenser without the center rod 32. In this case the gauze will be positioned in the same manner and will unroll relatively easily in the same manner. However, the ridge 48 is provided so that when the roll of gauze becomes rather small in unwinding and near the end of the roll, it is drawn up toward plate 48 and plate 48 keeps the roll from jamming as the roll will sit in the corner 45', beneath the plate 48 behind the channel 35, as it unrolls as illustrated in dashed lines in FIG. 1 and designated by nemeral 44".

Thus, it will be seen that a novel bandage or gauze dispenser has been provided which may be easily operated and rapidly separated to replace rolls of bandages or gauze.

It will be obvious that various changes and departures may be made to the invention without departing from the spirit and scope thereof and accordingly it is not intended that the invention be limited to that specifically described in the specification or as illustrated in the drawing but only as set forth in the claims wherein.

What is claimed is:

1. A bandage roll dispenser comprising a front and rear housing adapted to be mounted together, said front housing having a front wall with a horizontal channel at the top of the front wall, said front housing having cylindrical side discs mounted to the edges of the front wall, said rear housing having partial discs on each side stepped outward to overlap the rear half of the discs of the front housing, said rear housing having a curved cylindrical back wall, said rear housing having a top plate extending forward into the channel of the front housing, said roll of bandage within the front and rear housing, the outer end of the roll of bandage extends outward from within the front and rear housing between the channel and top plate of the front and rear housing to dispense the roll of bandage, said housing channel of said front housing has a raised ridge extending across the front housing channel to frictionally engage the gauze against the underside of the top portion to provide a drag on the gauze passing therethrough, said top plate, having a narrow horizontal ridge rearwardly projecting from the top plate and rearwardly projecting from the top of the front wall of the front housing providing a narrow ledge over the forward portion of the top of the front housing, so that as the roll of gauze becomes rather small, unwinding near the end of the roll, it will be drawn up against the ridge and the ridge helps to keep the roll from jamming.

2. A bandage roll dispenser according to claim 1, wherein said side discs of said front housing have slots extending into the center axis of the discs, whereby a rod may be inserted into the gauze and the rod inserted into the slots to support the roll of gauze in the housing.

* * * * *